United States Patent [19]

Cavalla et al.

[11] 4,045,444

[45] Aug. 30, 1977

[54] BENZAMIDO PIPERIDINES

[75] Inventors: John Frederick Cavalla, Isleworth; John Leheup Archibald, Windsor, both of England

[73] Assignee: John Wyeth & Brother Limited, Maidenhead, England

[21] Appl. No.: 678,772

[22] Filed: Apr. 20, 1976

Related U.S. Application Data

[63] Continuation-in-part of Ser. No. 564,509, April 2, 1975, Pat. No. 3,992,389, which is a continuation-in-part of Ser. No. 323,684, Jan. 15, 1973, abandoned, which is a continuation of Ser. No. 175,345, Aug. 26, 1971, abandoned.

[30] Foreign Application Priority Data

Sept. 3, 1970  United Kingdom ............... 42090/70
July 22, 1971  United Kingdom ............... 34376/71

[51] Int. Cl.$^2$ .................. C07D 405/06; C07D 405/12
[52] U.S. Cl. ............................................... 260/293.58
[58] Field of Search ................................... 260/293.58

[56] References Cited

U.S. PATENT DOCUMENTS 3,869,463  3/1975  Archibald ...................... 260/293.61
3,919,242  11/1975  Cavalla et al. .................. 260/293.58

*Primary Examiner*—Cecilia M. S. Jaisle
*Attorney, Agent, or Firm*—Arthur E. Wilfond

[57] ABSTRACT

A group of heterocyclic compounds useful in the treatment of disorders and diseases of the cardiovascular system is described. These compounds are piperidine compounds linked by the nitrogen atom to a methylenedioxyphenyl or an ethylenedioxyphenyl radical through the intermediary of a group selected from a mono-keto lower alkylene radical or a hydroxy-lower-alkylene radical or a bivalent radical of the formula

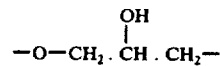

or —O—(lower alkylene). The piperidine rings are further substituted by a benzamido residue.

3 Claims, No Drawings

BENZAMIDO PIPERIDINES

This invention relates to heterocyclic compounds, to processes for their manufacture and to novel intermediates. This application is a continuation-in-part of U.S. Ser. No. 564,509, filed Apr. 2, 1975 now U.S. Pat. No. 3,992,389, patented Nov. 16, 1976, which in turn is a continuation-in-part of Ser. No. 323,684 filed Jan. 15, 1973 now abandoned, which was itself a continuation of Serial No. 175,345 filed August 26, 1971 and now abandoned.

In its broadest aspect the present invention provides a heterocyclic compound of the general formula

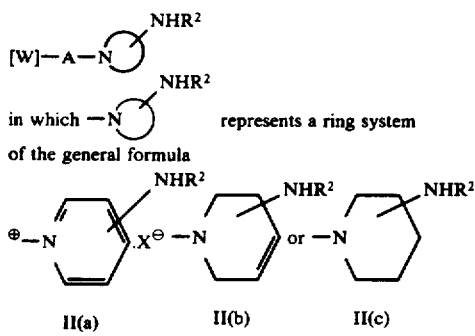

(I)

W represents a methylenedioxyphenyl or an ethylenedioxyphenyl radical, A represents a mono-keto lower alkylene radical, a hydroxy-lower-alkylene radical or a bivalent radical of the formula —O—CH$_2$CH(OH)CH$_2$— or O-(lower alkylene), R$^2$ represents the group -COR, where R represents a phenyl radical, X$^-$ is an anion, the term "lower" means that the radical contains from 1 to 6 carbon atoms, and the acid addition and quaternary ammonium salts of those compounds wherein is a ring system of formula II(b) or II(c).

It is to be understood that the term "alkylene" used herein includes both straight and branched chain radicals, the term "lower" means the radical concerned contains 1 to 6 carbon atoms, preferably 1 to 4 carbon atoms and by the term "aryl" radical is meant a radical possessing aromatic character.

The compounds of formula (I) which have a ring system of formula II(b) or II(c) wherein W and A are as defined above, R represents a phenyl radical and the pharmaceutically acceptable acid addition salts thereof exhibit pharmacological activity for example action on the cardiovascular system (particularly hypotensive and/or anti-hypertensive activity and α-adrenoceptor antagonist activity), and sometimes central nervous system activity (such as sedative activity) when tested on warm-blooded animals. The active compounds which have been prepared and tested have been found to possess action on the cardiovascular system.

In addition to having useful pharmaceutical properties as mentioned above the novel compounds of the invention are intermediates for the preparation of other compounds of formula I. The other compounds of the invention are also intermediates for the preparation of pharmacologically active compounds.

In a preferred aspect the invention provides a compound selected from the group consisting of (A) heterocyclic compounds of the formula

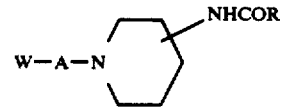

in which W represents a member of the group consisting of methylene- and ethylene-dioxyphenyl, A represents a bivalent radical selected from the group consisting of mono-keto lower alkylene, hydroxy lower alkylene, and radicals having the formdula —OCH$_2$CHOHCH$_2$— or O-lower alkylene; R represents phenyl, the term "lower" means that the radical contains from 1 to 6 carbon atoms; and (B) the pharmaceutically acceptable acid addition and quaternary ammonium salts thereof.

Preferably A has the formula CO(CH$_2$)$_n$ where n has the value from 1 to 3, the most preferred radical being —COCH$_2$CH$_2$CH$_2$—.

Examples of A are oxoethylene, oxo-butylene, hydroxyethylene and hydroxybutylene. Examples of acid addition salts are those formed from inorganic and organic acids in particular pharmaceutically acceptable acid addition salts such as the sulphate, hydrochloride, hydrobromide, hydro-iodide, nitrate, phosphate, sulphonate (such as the methane-sulphonate and p-toluene-sulphonate), acetate, maleate, fumarate, tartrate and formate.

The compounds of general formula (I) can be prepared in a number of ways by building up the molecule from suitable starting materials in known manner. Such processes applied to the preparation of the novel compounds of formula (I) are included in the scope of the invention.

One method of preparation of compounds of general formula(I) in which R$^2$ is the —COR group comprises reacting a compound of the general formula

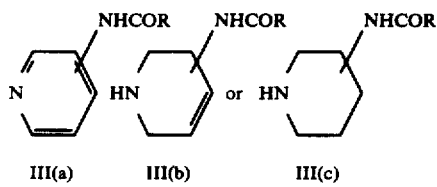

with an alkylating or acylating agent of the general formula

[W]-A-Y    (IV)

where R, W and A have the meanings already defined and Y is a halogen atom or an equivalent replaceable atom or radical, for example an organic sulphonyl radical such as tosyl radical. As an alternative, the compounds of formula III(b) or III(c) may be reacted with (i) a compound of the formula

[W]-A$^1$-H    (V)

wherein the chain A$^1$ contains an epoxide residue, for example (VI)

-continued

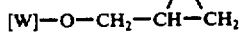

to give a compound of formula (I) wherein the chain A is substituted by a hydroxyl radical.

The compounds of general formulae (IV), (V) and (VI) are known compounds or can be made following the methods known for preparing compounds of these types. The starting materials of general formulae III(a), III(b) and III(c) can generally be made by acylating a corresponding amino compound of the general formula

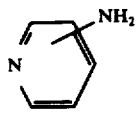

(VIII)

and if necessary reducing the ring system to the corresponding tetrahydropyridine or piperidine ring. The starting material of general formula III(c) is preferably prepared by either (i) forming the oxime of an N-benzyl-4-piperidone, reducing to give the 4-amino compound, acylating the amino group and then hydrogenolysing the benzyl residue, or (ii) treating the pyridine of formula

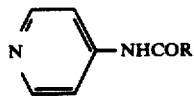

(IX)

with a benzyl halide, for example benzyl chloride to give the quaternary salt, reducing with an alkali metal borohydride to give the corresponding N-benzyl-tetrahydro-pyridine which is further subjected to concomitant de-benzylation and reduction of the 3,4-double bond by catalytic hydrogenation, or (iii) catalytic hydrogenation of compound (IX) in the presence of acetic anhydride to give

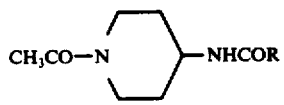

(X)

and then selectively hydrolysing the acetyl group.

A second general method of preparation of compounds of formula (I) in which $R^2$ is the —COR group, comprises reacting a compound of formula (I) in which $R^2$ is a hydrogen atom, with either a reactive derivative of an acid of general formula R.COOH (where R is aryl, or cycloalkyl). As a reactive derivative of the acid of formula R.COOH used in the process described above, we have found it preferable usually to use a halide (for example the chloride or bromide) or an anhydride. Other examples of reactive derivatives of the acid R.COOH which may be used are the acid azide, mixed anhydrides and active esters. Furthermore, the compounds of formula (I) in which $R^2$ is the —COR group may also be prepared by treating a compound of formula (I) in which $R^2$ is a hydrogen atom with the acid R.COOH in the presence of a known condensing agent (for example, a carbodiimide), or by first activating the amino function (for example, by forming the phosphazo derivative) and then reacting with the acid R.COOH. In connection with the introduction of the —COR group into a compound of formula (I) in which $R^2$ is a hydrogen atom, reference may be made to "Chemistry of the Amino Acids" by Greenstein and Winitz (John Wiley & Sons. Inc. Publishers, 1961) at pages 782-883 and 943-1108).

When the compounds of general formula (I) are desired in which

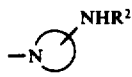

represents a ring system of formula II(b) or II(c), $R^2$ is the —COR group and A is a mono-keto lower alkylene radical the preparation may comprise a Mannich reaction using formaldehyde, a compound of formula III(b) or III(c) as secondary amine and either a compound WH, where W has the meanings already defined and thus WH can be considered as a compound formed by addition of a hydrogen atom to said radical W; said compound WH also containing a suitable reactive site of the type known in the literature to participate in the Mannich reaction, or a derivative of W (as just defined) in which the chain A has already been partially formed, and which partially formed chain contains a site of the type known in the literature to participate in the Mannich reaction. Examples of the latter type of derivative are [W]-CO.CH₃ which derivatives are known compounds or can be made following the methods known for preparing compound of these types. The formaldehyde used in the above reaction may be in the form of a solution in an inert solvent or as a paraformaldehyde.

When it is desired to prepare a compound of general formula (I) wherein $R^2$ is a hydrogen atom, a corresponding compound of formula

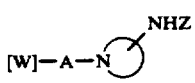

(XII)

(wherein W, has the meaning defined in connection with formula (I),

represents a ring system of formula

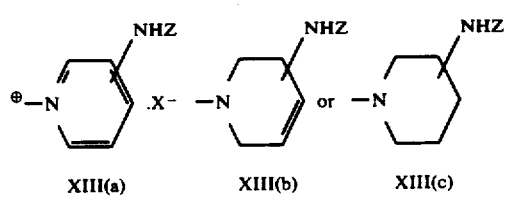

and Z is a protecting group known in the art for the protection of the amino function and A has the meanings defined immediately above), is subjected to hydrolysis, hydrogenolysis or some other reaction known in the art for the removal of the protecting group Z. As example of Z, mention is made of those wherein Z is the group —COR and R is lower alkyl, lower alkoxy and aryloxy (particularly methyl, ethoxy and phenoxy respectively) or aryl. Other examples of Z are benzyl, p-toluene-sulphonyl, phthalyl, trityl, trifluoroacetyl, formyl and benzyl-sulphonyl. Reference may be made to the review of protecting groups in Advances in Organic Chemistry, 3, 191–294 (Interscience Publishers 1963), and also to Chemistry of the Amino Acids by Greenstein and Winitz, Vol. 2, pages 885–924 (John Wiley & Sons, Inc., 1961). The compounds of general formula (XII) can be prepared following the information already given but using the appropriate acylating agent or other reagent to introduce the group Z.

In order to prepare a compound of formula (I) in which

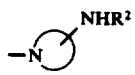

represents a ring system of formula II(b) or II(c), W has the meanings defined in connection with formula (I), $R^2$ is the —COR group wherein R has the meanings defined in connection with formula (I) and A is a mono-keto lower-alkylene radical of formula —CO.(CH$_2$)$_m$— in which m is 1 to 5, a compound of formula

[W]-H            (XVII)

can be acylated (Friedel-Crafts) with an acid halide of formula

(XVIII)

For details of the reaction, reference may be made to "The Friedel-Crafts and related Reactions", by G.A. Olah, Vol. 2 (Interscience Publishers, 1964).

The reactions outlined above usually are carried out in a solvent which is inert under the reaction conditions. The most suitable solvent system is chosen and varies depending on the particular reactants being employed. If necessary heating the reactants in solution under reflux can be carried out, and if necessary heating under high pressures may also be used.

Once a compound of general formula (I) has been prepared, then if necessary one or more substituents in the molecule may be converted to another substituent each within its own meanings specified in connection with formula (I). If a compound is produced in which

represents the pyridinium ring system of formula II(a), this may be selectively reduced to one of the other ring systems of lower oxidation state. For example, reduction with an alkali metal borohydride gives the tetrahydropyridine ring system of formula II(b). On the other hand, catalytic hydrogenation, for example, in the presence of Raney Nickel or a platinum catalyst, gives rise to the piperidine ring system of formula II(c). Similarly, if a compound of formula (I) is prepared in which

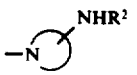

represents the tetrahydropyridine ring system of formula II(b), this may also be reduced to the piperidine ring system of formula II(c).

If a compound of formula (I) is prepared in which the chain A contains one or more carbonyl functions, then this chain may be selectively reduced. For example, when A is the oxalyl residue —CO.CO—, this may be reduced under mild conditions such as by a hydride transfer agent (particularly lithium aluminium hydride) to give the

residue. When A is the —CO—CH$_2$—residue this may be reduced with an alkali metal borohydride to give the

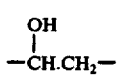

residue. When the oxalyl residue is reduced under more drastic conditions, the ethylene chain —CH$_2$—CH$_2$— results.

If a compound of formula (I) is produced in which $R^2$ is the —COR group, if necessary this may be hydrolysed to the compound of formula (I) in which $R^2$ is a hydrogen atom and which may then be reacted to give a compound of formula (I) in which $R^2$ is a different —COR group.

Compounds of formula I in which A contains a hydroxy group i.e. hydroxy-lower-alkylene or —O—CH$_2$CH(OH)CH$_2$, or wherein A is a branched chain radical possess an asymmetric carbon atom and are therefore capable of existing in optically active stereo isomeric forms. The optical isomers may be separated by standard resolution procedures. For instance compounds such as those which contain the ring system of formula II(b) or II(c) contain a basic nitrogen atom and may generally be resolved by treatment with a suitable optically active acid. Optically active acids are described in the literature and suitable ones for the resolution of any particular compound are chosen by experiment.

If necessary, in any of the reactions hereinbefore described, reactive substituent groups may be blocked during a reaction and released at a later stage. As already indicated the novel tetrahydropyridine and piperidine compounds provided by the invention contain a basic nitrogen atom and thus can form acid addition salts with acids (particularly pharmaceutically acceptable acids) or quaternary ammonium salts, for example with alkyl halides or aralkyl halides (particularly methyl iodide or benzyl chloride or bromide). The acid addition salts may either be formed in situ during the hereinbefore described processes and isolated therefrom or a free base may be treated with the appropriate acid in the presence of a suitable solvent and then the salt isolated. The quaternary salts may be prepared by treating the free base with the appropriate halide in the presence or absence of a solvent.

As already mentioned, the pharmaceutical compositions of the invention contain as active ingredients a compound of formula (I) as hereinbefore defined, which may be micronised. In addition to the active ingredient, said compositions also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier which is thus in association with it. Similarly cachets are included.

Sterile liquid form compositions include sterile solution, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The following non-limiting Examples illustrate the invention. Examples 1 and 2 are reference Examples. The remaining Examples illustrate the invention:

EXAMPLE 1 (Reference example)

4-Benzamido-1-[4-(4-methoxyphenyl)-4-oxobutyl]-piperidine

4-Benzamidopiperidine (4.086 g., 0.02 mole), 4-(4-chloro-1-oxobutyl)methoxybenzene (4.245 g., 0.02 mole) and finely ground anhydrous potassium carbonate (4.146 g., 0.03 mole) were mixed and heated on a steam bath for one hour. The solid obtained was stirred in water at 60° for one hour, the title compound was filtered off, washed well with water and ether to give 3.82 g. This was dissolved in hot absolute ethanol, the solution was acidified with ethanolic hydrogen chloride and cooled to give the hydrochloride of the title compound (3.54 g., 41%) m.p. 224.8°.

$C_{23}H_{28}N_2O_3.HCl.H_2O$ requires C, 63.51; H, 7.18; N, 6.44: Found: C, 63.50; H, 6.84; N, 6.35%.

The product exhibited hypotensive activity in standard test procedures.

EXAMPLE 2 (reference example)

1-[4-(1′,2′,3′,4′-Tetrahydro-6′-naphthyl)-4-hydroxybutyl]-4-benzamidopiperidine 1-[4-(1′,2′,3′,4′-tetrahydro-6′-naphthyl)-4-oxobutyl]-4-benzamidopiperidine (4.046 g., 0.01 mole) was dissolved in methanol (500 ml.) at 15° C, and while stirring a solution of sodium borohydride (10.0 g.) in 0.2 N sodium hydroxide solution (200 ml.) was added over 1 hour. The reaction mixture was stirred at room temperature for 20 hours, refluxed for 2 hours and filtered while hot. The methanol was distilled from the filtrate and the title compound crystallised out. This was converted to the hydrochloride by passing hydrogen chloride gas into a solution in methanol until acid and adding ethyl acetate and ether to precipitate the salt. The yield in two crops was 3.715 g., (84%) m.p. 238.9°. $C_{26}H_{34}N_2O_2.HCl.1/4.H O$ requires C, 69.79; H,8.00; N, 6.26. Found: C, 69.85; H, 8.12; N, 6.38%.

The product exhibited hypotensive activity in a standard test procedure.

EXAMPLE 3

1-[3-(1,4-Benzodioxan-6-yl)-3-oxopropyl]-4-benzamidopiperidine

Using the procedure of Example 1, for a longer period of 20 hours, 4-benzamidopiperidine (1.022 g., 0.005 mole) was alkylated with 3-chloro-1-(1,4-benzodioxan-6-yl)propan-1-one (1.134 g., 1 equivalent) to give 1.433 g. of the crude base after washing with water and ether. Conversion of this to the hydrochloride by treatment with ethanolic hydrogen chloride and ether gave the title compound as the hydrochloride quater hydrate (1.425 g., 65.5%) m.p. 198.1°. $C_{23}H_{26}N_2O_4.HCl.1/4 H_2O$ requires C, 63.46; H, 6.37; N, 6.43; Found: C, 63.49; H, 6.57; N, 6.56%. The product exhibited hypotensive activity in a standard test procedure.

EXAMPLE 4

1-[3-(1,4-Benzodioxan-6-yl)-3-hydroxypropyl]-4-benzamido piperidine

Using the procedure of Example 2 1-[3-(1,4-benzodioxan-6-yl)-3-oxopropyl]-4-benzamidopiperidine (5.918 g., 0.015 mole) was reduced to the title compound subsequently obtained as the hydrochloride (3.155 g., 48.6%) m.p. 193°–7°. $C_{23}H_{28}N_2O_4.HCl$ requires C,63.81; H, 6.75; N,6.47. Found: C, 63.63; H, 6.89; N, 6.24%.

The product exhibited hypotensive activity in a standard test procedure.

EXAMPLE 5

1-[4-(3',4'-methylenedioxy-phenyl)-4-oxobutyl]-4-benzamidopiperidine

Using the procedure of Example 1, 4-benzamidopiperidine is alkylated with 4'-chloro-1'-oxobutyl-3,4-methylenedioxy-benzene to give the title compound.

EXAMPLE 6

4-Benzamido-1-[2-(3',4'-methylenedioxy)phenoxyethyl]-piperidine

Using the procedure of Example 1, 4-benzamidopiperidine is alkylated with 2-(3',4'-methylenedioxyphenoxy)ethyl chloride to give the title compound.

EXAMPLE 7

4-Benzamido-1-[3-(3',4'-methylenedioxyphenoxy)-2-hydroxypropyl]piperidine

Using the procedure of Example 1, 4-benzamidopiperidine is alkylated with 3-(3',4'-methylenedioxyphenoxy)-2-hydroxypropyl chloride to give the title compound.

The invention includes a method of relieving disorders and diseases of the cardiovascular system in a mammal which comprises administering to said mammal a therapeutically effective amount of hetercyclic compound of general formula (I)

in which

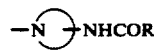

represents a ring system of general formula

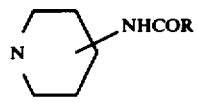

W represents a carbocyclic aryl radical selected from ethylenedioxyphenyl or methylenedioxyphenyl, A represents a keto lower alkylene radical, a hydroxy-loweralkylene radical or a bivalent radical of the formula —O—CH$_2$CH(OH)CH$_2$ or —O—(lower alkylene), R represents phenyl radical, the term "lower" means that the radical contains from 1 to 6 carbon atoms, and the pharmaceutically acceptable acid addition salts thereof.

Tests for action on the cardiovascular system were conducted according to one of the following procedures:

HYPOTENSIVE AND/OR ANTI-HYPERTENSIVE ACTIVITY

Method 1 (Rat)

Rats were anaesthetised with pentobarbitone sodium (60 mg/kg) and the jugular vein, trachae and carotid artery were cannulated. The test compound was given intravenously at 15 min. intervals (dose range 0.8-25.6 mg/kg cumulative) and blood pressure and heart rate were recorded via the carotid artery at 30 second and 15 minutes after administration. The production of a fall of 30 mm.mercury in diastolic pressure from control values was considered to be significant hypotensive activity. A decrease in heart rate of more than 30% from control values was considered to be significant bradycardia.

Method 1 (Cat)

Cats were anaesthetised with pentobarbitone sodium (30 mg/kg) and the cephalic vein, femoral and carotid arteries and trachae were cannulated. The carotid cannula was introduced into the left ventricle and the femoral cannula into the aorta. Blood pressure and heart rate were recorded from the artic cannula and left ventricular pressure from the carotid cannula. The test compounds were administered intravenously (0.1- 25.6 mg/kg).

Method 2 (hypertensive rats

Male or female rats are rendered hypertensive by applying a figure of 8 ligature around one kidney and contralateral nephrectomy. Blood pressure stabilises at a hypertensive level after 6 weeks. Systolic pressure is measured indirectly using a Decker Caudal Plethysmograph. A control group of rats is run with each group treated with drug. Each group usually consists of six rats. Drugs are usually administered by the IP or oral routes. Pressures are read prior to drug administration and at two and 24 hours thereafter.

α-Adrenoceptor Antagonism Activity

Carried out on the guinea pig aortic strip [Furchgott and Bhadrakom (1953) J. Pharmac, exp. Ther.108, 129-143] by the method of Alps et al [Br. J. Pharmac.1972 44, 52-62].

In this test the compound of Example 4 had a pA$_2$ of 6.6

Activity in either method 1 (rats of cats) or method 2 was considered to indicate hypotensive activity.

TABLE

| Compound of Example | Hypotensive Activity a | Anti-hypertensive Activity b |
|---|---|---|
| Example 3 | + | |
| Example 4 | + + + | + |

Key: a Cumulative IV doses producing a fall in diastolic blood pressure of 30 mm or more, sustained for at least 15 minutes:
1.6 or 3.2 mg/kg + + +, 6.4 or 12.8 mg/kg + +;
25.6 mg/kg +. b Falls in systolic blood pressure 2 hours after an oral dose of 40 mg/kg.
30-15 mm, +.

The Specification of U.S. application Ser. No. 564,509, filed Apr. 2, 1975 is hereby incorporated herein by reference.

We claim:

1. A compound selected from the group consisting of
A. heterocyclic compounds of the formula

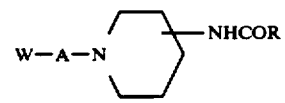

in which W represents a member of the group consisting of 3,4 methylene- or 3,4 ethylene-dioxyphenyl, A represents a bivalent radical selected from the group consisting of mono-keto lower alkylene, hydroxy lower alkylene and radicals having the formula —OCH$_2$CHOHCH$_2$ or —O— loweralkylene, R represents phenyl and the term "lower" means that the radical contains from 1 to 6 carbon atoms and (B) the pharmaceutically acceptable acid addition and quaternary ammonium salts thereof.

2. A compound as claimed in claim 1, which is 1-[3-(1,4-benzodioxan-6-yl)-3-oxopropyl]-4-benzamidopiperidine or a pharmaceutically acceptable acid addition salt thereof.

3. A compound as claimed in claim 1, which is 1-[3-(1,4-benzodioxan-6-yl)-3-hydroxypropyl]-4-benzamidopiperidine or a pharmaceutically acceptable acid addition salt thereof.

* * * * *